United States Patent [19]
Aceves

[11] Patent Number: 6,126,621
[45] Date of Patent: Oct. 3, 2000

[54] CAST COVERING APPARATUS

[76] Inventor: Santiago Aceves, 4108 Ravenwood Ct. Northwest, Albuquerque, N. Mex. 87107

[21] Appl. No.: 09/328,997

[22] Filed: Jun. 10, 1999

[51] Int. Cl.[7] .................................................. A61F 5/00
[52] U.S. Cl. ................................................ 602/3; 128/878
[58] Field of Search ............................. 602/3, 5, 20, 23; 128/878, 846, 877, 879

[56] References Cited

U.S. PATENT DOCUMENTS

| 4,178,924 | 12/1979 | Baxter . |
| 5,063,919 | 11/1991 | Silverberg . |
| 5,720,712 | 2/1998 | Joy et al. . |

*Primary Examiner*—Michael A. Brown
*Assistant Examiner*—Lalita M. Hamilton

[57] ABSTRACT

A cast covering apparatus for effectively and comfortably covering an extremity of the body includes a cover member having a cuff assembly at an open end, an absorbent interior layer, and a plurality of cinch assemblies.

18 Claims, 4 Drawing Sheets

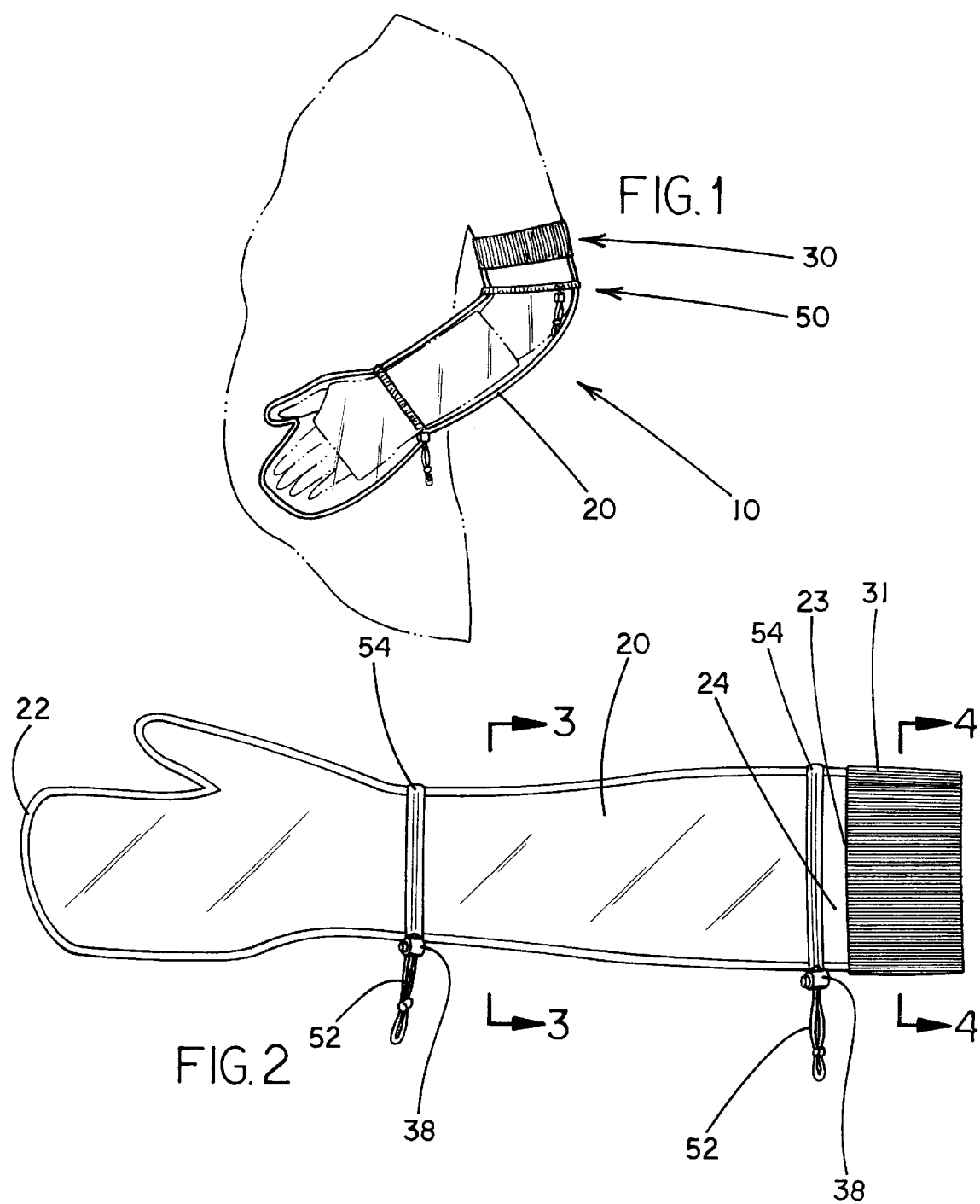

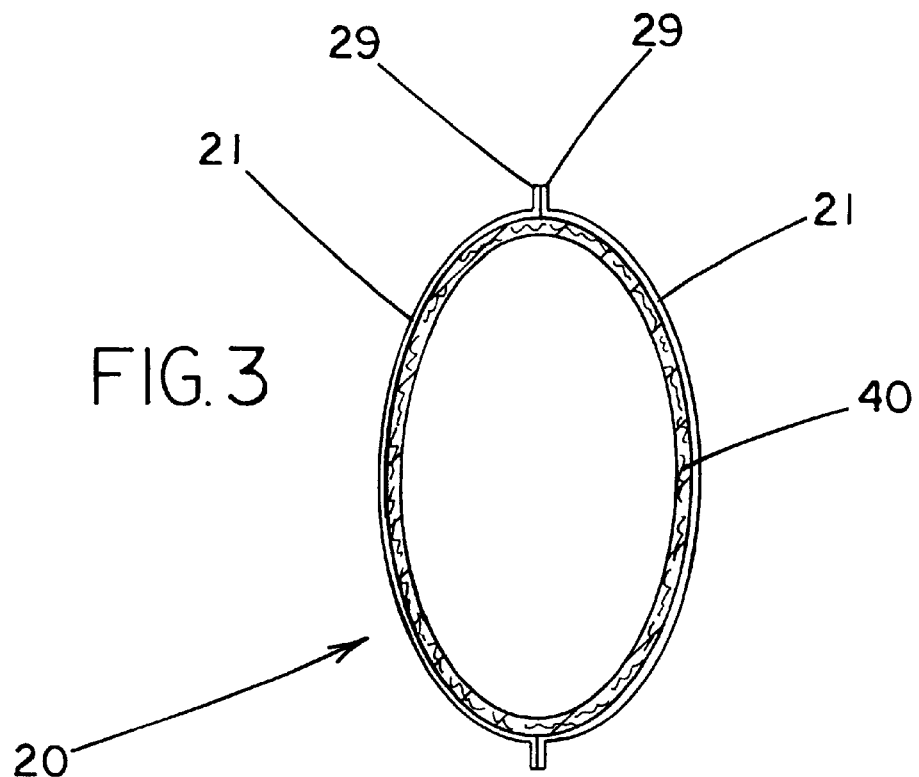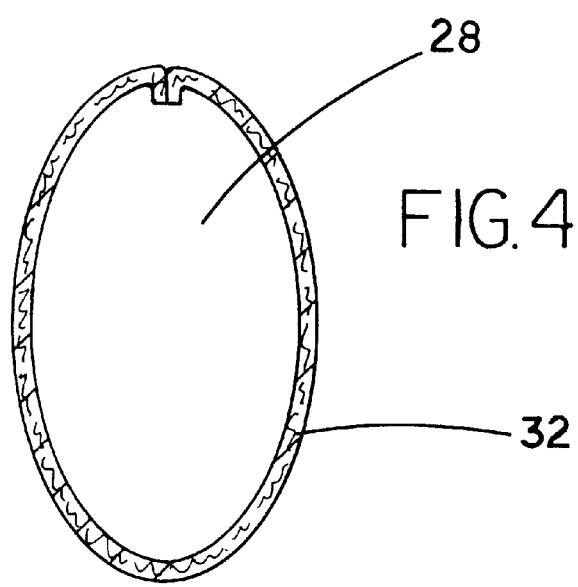

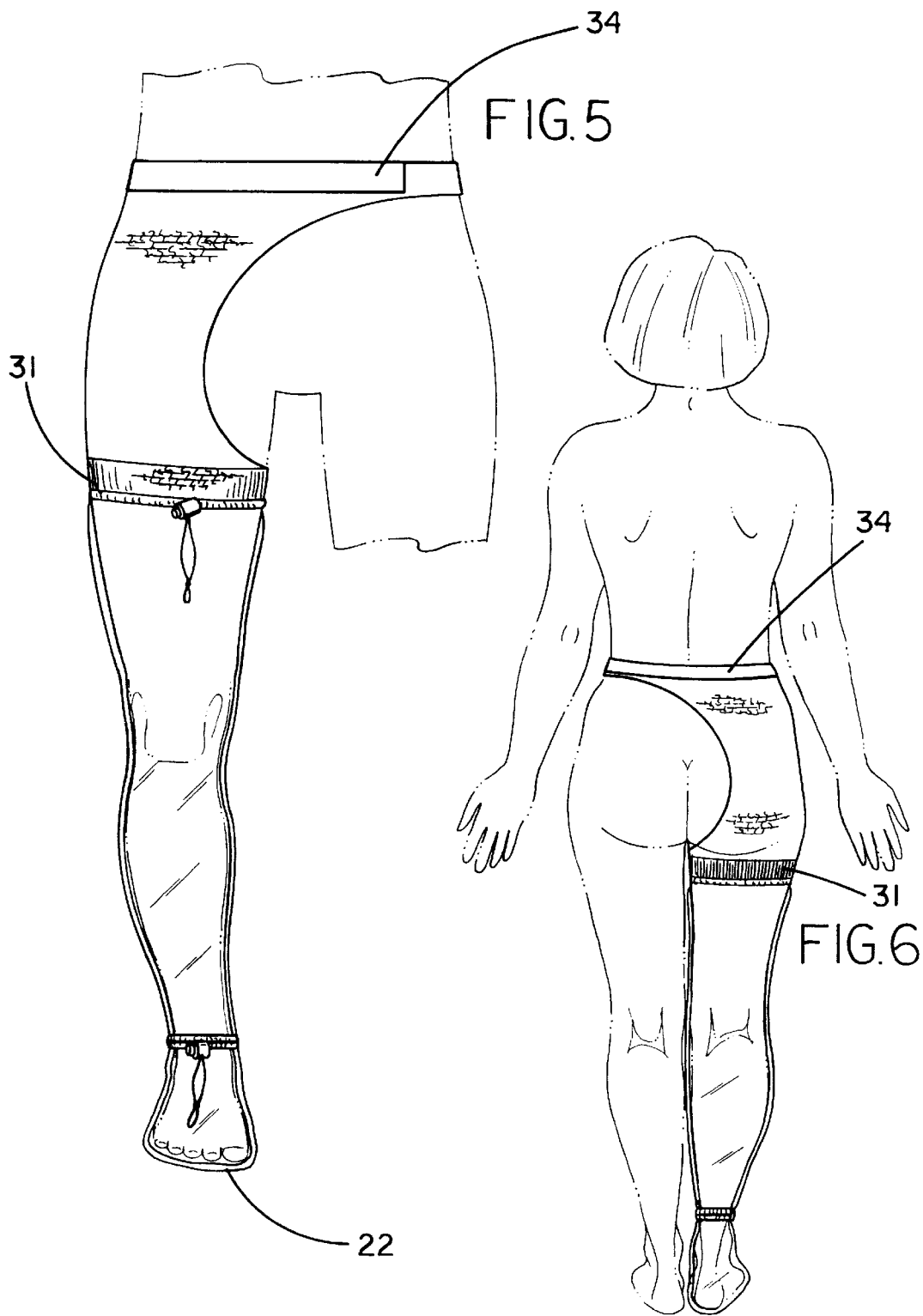

CAST COVERING APPARATUS

BACKGROUND OF THE INVENTION

1. Field of the Invention

The present invention relates to wound and cast covers and more particularly pertains to a new cast covering apparatus for effectively and comfortably covering an extremity of the body.

2. Description of the Prior Art

The use of wound and cast covers is known in the prior art. More specifically, wound and cast covers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,741,203; U.S. Pat. No. 4,986,265; U.S. Pat. No. Des. 340,115; U.S. Pat. No. 4,036,330; U.S. Pat. No. 4,346,699; and U.S. Pat. No. 4,911,151.

While these devices fulfill their respective, particular objectives and requirements, the aforementioned patents do not disclose a new cast covering apparatus. The inventive device includes a cover member having a cuff assembly at an open end, an absorbent interior layer, and a plurality of cinch assemblies.

In these respects, the cast covering apparatus according to the present invention substantially departs from the conventional concepts and designs of the prior art, and in so doing provides an apparatus primarily developed for the purpose of effectively and comfortably covering an extremity of the body.

SUMMARY OF THE INVENTION

In view of the foregoing disadvantages inherent in the known types of wound and cast covers now present in the prior art, the present invention provides a new cast covering apparatus construction wherein the same can be utilized for effectively and comfortably covering an extremity of the body.

The general purpose of the present invention, which will be described subsequently in greater detail, is to provide a new cast covering apparatus apparatus and method which has many of the advantages of the wound and cast covers mentioned heretofore and many novel features that result in a new cast covering apparatus which is not anticipated, rendered obvious, suggested, or even implied by any of the prior art wound and cast covers, either alone or in any combination thereof.

To attain this, the present invention generally comprises a cover member having a cuff assembly at an open end, an absorbent interior layer, and a plurality of cinch assemblies.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new cast covering apparatus apparatus and method which has many of the advantages of the wound and cast covers mentioned heretofore and many novel features that result in a new cast covering apparatus which is not anticipated, rendered obvious, suggested, or even implied by any of the prior art wound and cast covers, either alone or in any combination thereof.

It is another object of the present invention to provide a new cast covering apparatus that may be easily and efficiently manufactured and marketed.

It is a further object of the present invention to provide a new cast covering apparatus that is of a durable and reliable construction.

An even further object of the present invention is to provide a new cast covering apparatus which is susceptible of a low cost of manufacture with regard to both materials and labor, and which accordingly is then susceptible of low prices of sale to the consuming public, thereby making such cast covering apparatus economically available to the buying public.

Still yet another object of the present invention is to provide a new cast covering apparatus which provides in the apparatuses and methods of the prior art some of the advantages thereof, while simultaneously overcoming some of the disadvantages normally associated therewith.

Still another object of the present invention is to provide a new cast covering apparatus for effectively and comfortably covering an extremity of the body.

Yet another object of the present invention is to provide a new cast covering apparatus which includes a cover member having a cuff assembly at an open end, an absorbent interior layer, and a plurality of cinch assemblies.

Still yet another object of the present invention is to provide a new cast covering apparatus that covers an entire cast positioned on an extremity of the human body.

Even still another object of the present invention is to provide a new cast covering apparatus that prevents water and other contaminants from contacting a cast on the human body.

Even yet another object of the present invention is to provide a cast covering apparatus that has adjustable tightness along a length of the cover apparatus for maximizing fit and comfort of the user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of a new cast covering apparatus according to the present invention.

FIG. 2 is a schematic front view of the present invention.

FIG. 3 is a schematic cross-sectional view of the present invention taken along line 3—3 of FIG. 2.

FIG. 4 is a schematic cross-sectional view of the present invention taken along line 4—4 of FIG. 2.

FIG. 5 is a schematic front view of an embodiment of the present invention.

FIG. 6 is a schematic rear view of an embodiment of the present invention.

DESCRIPTION OF THE PREFERRED EMBODIMENT

Figure 7:
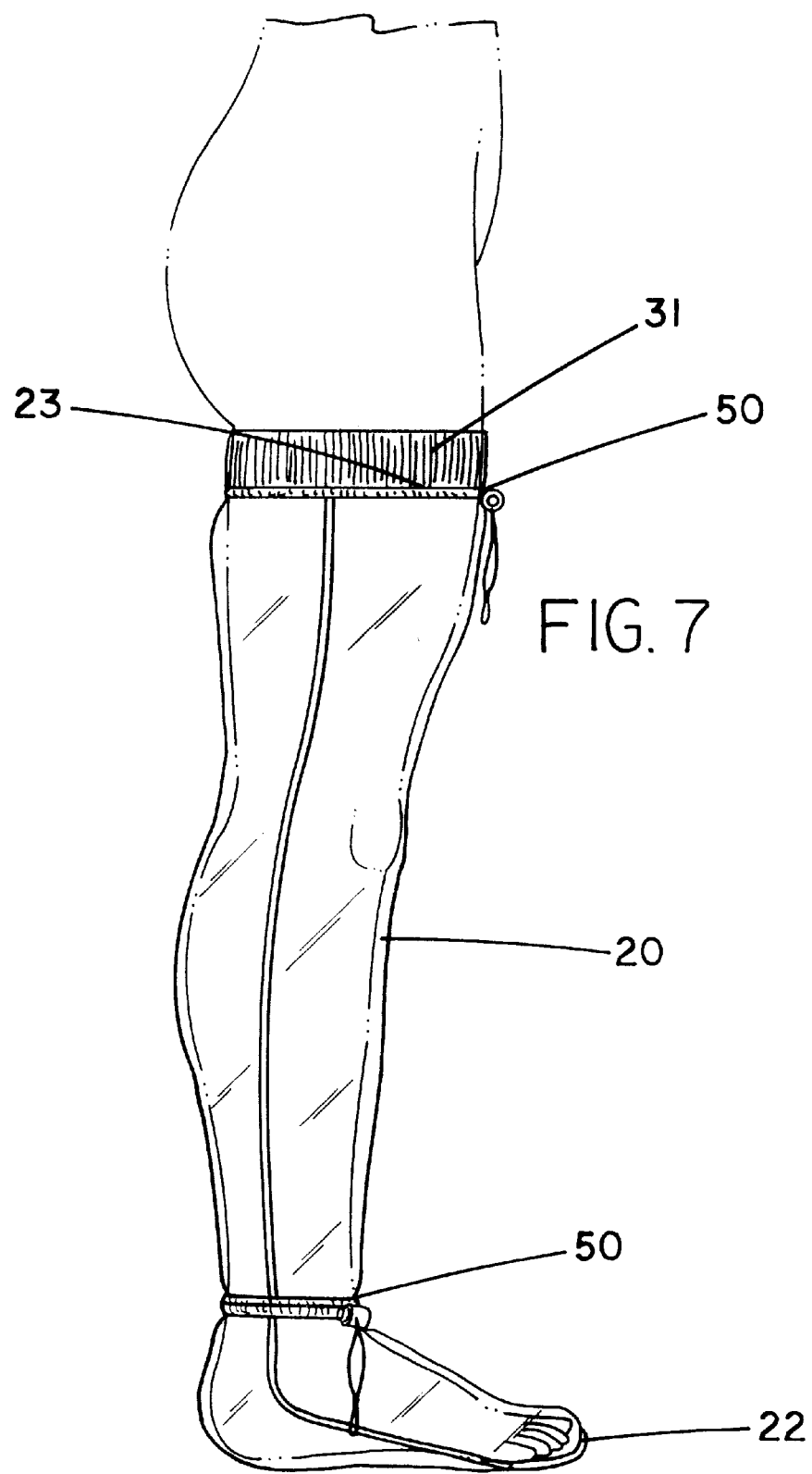
FIG. 7 is a schematic side view of an embodiment of the present invention.

With reference now to the drawings, and in particular to FIG. 1 through 7 thereof, a new cast covering apparatus embodying the principles and concepts of the present invention and generally designated by the reference numeral 10 will be described.

As best illustrated in FIGS. 1 through 7, the cast covering apparatus 10 generally comprises a flexible cover member 20, a cuff assembly 30, a liner 40, and a number of cinch assemblies 50.

The cover member has a first end 22 and a second end 24 opposite the first end. The first end is closed and the second end includes an opening 28 into an interior of the cover member. The opening includes a perimeter edge 29. Optionally, the cover member is formed by joining two cover portions 21 around the absorbent liner with the two cover portions being joined to each other along an outer perimeter 23 of each cover portion.

A cuff assembly 30 is coupled to the perimeter edge 29. The cuff assembly is an elastic material 32 designed to form a cuff 31 to snugly surround a portion of an extremity of the user's body. Thus, the cuff 31 is designed to hold itself and the cover member in a generally static position relative to the extremity of the human body such that the cover member does not fall off the user.

Optionally, an adjustment strap 34 is coupled to the cuff. The adjustment strap is designed for wrapping around a part of the user's body to facilitate secure positioning of the cuff relative to the user's body. The adjustment strap may be secured to itself using hook and loop fasteners applied to portions of the strap or other conventional securing devices may be used such as clips or buckles. Optionally, the strap is coupled to a distal edge of the cuff and may be wrapped around the cuff or extend away from the cuff to a remote portion of the body for holding the cuff in position. As shown in an optional embodiment in FIGS. 5 and 6, the cuff surrounds the upper thigh and the strap extends away and around the waist of the user.

The absorbent liner is positioned within the interior of the cover member and optionally extends a full length of the cover member or a partial distance along the length of the cover member.

Multiple cinch assemblies may be employed along a length of the cover member. Optionally a pair of cinch assemblies are positioned in spaced relationship along a length of the cover member. Each of the cinch assemblies is positioned proximate a respective end of the cover member. Each cinch assembly includes a cinch line 52 positioned around the cover member for tightening around the cover member. The cinch line is oriented substantially transverse to a longitudinal axis of the cover member. A cinch line cover 54 substantially encloses the cinch line. The cinch line cover is coupled to the cover member for preventing the cinch line from moving along a length of the cover member. The cinch line includes opposite ends 53 extending outside the cinch line cover for adjustable securing to hold the cinch line with a selectable degree of tightness around the cover member. Optionally, a clip member 38 is used for adjustably holding the opposite ends of the cinch line whereby the cinch line is maintainable in a tightened position.

Depending on the extremity being covered, the first end is designed to receive a hand or a foot. Optionally, the first end may be configured to accommodate fingers and toes for maximum comfort to the user and to suit personal preferences of the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A cast covering apparatus, comprising:

a flexible cover member having a first end and a second end opposite the first end;

said first end being closed;

said second end having an opening into an interior of said cover member, said opening having a perimeter edge;

a cuff assembly coupled to said perimeter edge;

an absorbent liner positioned within said interior of said cover member, said absorbent liner extending continuously in the longitudinal direction within said interior of said cover member adjacent to an inner surface of said cover member; and a plurality of cinch assemblies positioned in spaced relationship along a length of said cover member.

2. The cast covering apparatus of claim 1, further comprising:

said cuff assembly including a cuff;

said cuff being an elastic material adapted to snugly surround a portion of an extremity of the user's body whereby said cuff is adapted to be held in a static position relative to the extremity of the human body.

3. The cast covering apparatus of claim 2, further comprising:

an adjustment strap being coupled to said cuff, said adjustment strap being adapted for wrapping around a part of the user's body to facilitate secure positioning of the cuff relative to the user's body.

4. The cast covering apparatus of claim 3 further comprising:

said cuff being adapted for snugly engaging an arm of the user; and said strap configured for wrapping around an outer surface of said cuff.

5. The cast covering apparatus of claim 3, further comprising:

said adjustment strap including an extension portion positioned between a distal edge of said cuff and a distal portion of said strap;

said cuff being adapted for snugly surrounding a thigh of the user; and said strap extending from a distal edge of said extension portion whereby said strap is adapted for wrapping around a waist of the user in spaced relationship to said cuff for supporting said cuff.

6. The cast covering apparatus of claim 1, wherein each cinch assembly comprises:

a cinch line positioned around said cover member, said cinch line being for tightening around said cover member, said cinch line being substantially transverse to a longitudinal axis of said cover member;

a cinch line cover substantially enclosing said cinch line, said cinch line cover being coupled to said cover member for preventing said cinch line from moving along a length of said cover member, said cinch line having opposite ends extending outside said cinch line cover whereby said cinch line opposite ends are securable to hold said cinch line with a selectable degree of tightness around said cover member.

7. The cast covering apparatus of claim 6, further comprising:

a clip member, said opposite ends of said cinch line passing through said clip member, said clip member being selectively engageable to said opposite ends of said cinch line for adjustably holding said opposite ends of said cinch line whereby said cinch line is maintainable in a tightened position at a selectable degree of tightness of said cinch line around said cover member.

8. The cast covering apparatus of claim 7, further comprising:

said cover member being formed by joining two cover portions around said absorbent liner, said two cover portions being joined to each other along an outer perimeter of each cover portion.

9. The cast covering apparatus of claim 7, wherein said first end is configured such that said first end is adapted to receive one of the body parts chosen from the group of body parts consisting of a hand and a foot.

10. The cast covering apparatus of claim 7, further comprising:

said cuff assembly including a cuff;

said cuff being an elastic material adapted to snugly surround a portion of an extremity of the user's body whereby said cuff is adapted to be held in a static position relative to the extremity of the human body.

11. The cast covering apparatus of claim 10, further comprising:

an adjustment strap being coupled to said cuff, said adjustment strap being adapted for wrapping around a part of the user's body to facilitate secure positioning of the cuff relative to the user's body.

12. The cast covering apparatus of claim 11, further comprising:

said cuff being adapted for snugly engaging an arm of the user; and said strap configured for wrapping around an outer surface of said cuff.

13. The cast covering apparatus of claim 11, further comprising:

said adjustment strap including an extension portion positioned between a distal edge of said cuff and a distal portion of said strap;

said cuff being adapted for snugly surrounding a thigh of the user; and said strap extending from a distal edge of said extension portion whereby said strap is adapted for wrapping around a waist of the user in spaced relationship to said cuff for supporting said cuff.

14. The cast covering apparatus of claim 1, further comprising:

said cover member being formed by joining two cover portions around said absorbent liner, said two cover portions being joined to each other along an outer perimeter of each cover portion.

15. The cast covering apparatus of claim 1, wherein said first end is configured such that said first end is adapted to receive one of the body parts chosen from the group of body parts consisting of a hand and a foot.

16. A cast covering apparatus, comprising:

a flexible cover member having a first end and a second end opposite the first end;

said first end being closed;

said second end having an opening into an interior of said cover member, said opening having a perimeter edge;

a cuff assembly coupled to said perimeter edge;

an absorbent liner positioned within said interior of said cover member, said absorbent liner extending continuously in the longitudinal direction within said interior of said cover member adjacent to an inner surface of said cover member;

a pair of cinch assemblies positioned in spaced relationship along a length of said cover member, each of said cinch assemblies being positioned proximate a respective end of said cover member;

said cuff assembly including a cuff, said cuff being an elastic material adapted to snugly surround a portion of an extremity of the user's body whereby said cuff is adapted to be held in a static position relative to the extremity of the human body;

an adjustment strap being coupled to said cuff, said adjustment strap being adapted for wrapping around a part of the user's body to facilitate secure positioning of the cuff relative to the user's body;

wherein each cinch assembly includes a cinch line positioned around said cover member, said cinch line being for tightening around said cover member, said cinch line being substantially transverse to a longitudinal axis of said cover member;

a cinch line cover substantially enclosing said cinch line, said cinch line cover being coupled to said cover member for preventing said cinch line from moving along a length of said cover member, said cinch line having opposite ends extending outside said cinch line cover whereby said cinch line opposite ends are securable to hold said cinch line with a selectable degree of tightness around said cover member;

a clip member, said opposite ends of said cinch line passing through said clip member, said clip member being selectively engageable to said opposite ends of said cinch line for adjustably holding said opposite ends of said cinch line whereby said cinch line is maintainable in a tightened position at a selectable degree of tightness of said cinch line around said cover member;

said cover member being formed by joining two cover portions around said absorbent liner, said two cover portions being joined to each other along an outer perimeter of each cover portion; and wherein said first end is configured such that said first end is adapted to receive one of the body parts chosen from the group of body parts consisting of a hand and a foot.

17. The cast covering apparatus of claim 16, further comprising:

said first end being adapted to receive a hand;

said cuff being adapted for snugly engaging an arm of the user; and said strap configured for wrapping around an outer surface of said cuff.

18. The cast covering apparatus of claim 16, further comprising:

said first end being adapted to receive a foot;

said adjustment strap including an extension portion positioned between a distal edge of said cuff and a distal portion of said strap;

said cuff being adapted for snugly surrounding a thigh of the user; and said strap extending from a distal edge of said extension portion whereby said strap is adapted for wrapping around a waist of the user in spaced relationship to said cuff for supporting said cuff.

* * * * *